United States Patent [19]
Parins

[11] Patent Number: 6,152,924
[45] Date of Patent: Nov. 28, 2000

[54] BIPOLAR BIOPSY FORCEPS

[76] Inventor: David J. Parins, 6801 Olde Sturbridge Dr., Corcoran, Minn. 55340

[21] Appl. No.: 09/404,694

[22] Filed: Sep. 24, 1999

[51] Int. Cl.[7] .................................................... A61B 17/00
[52] U.S. Cl. ............................ 606/52; 606/174; 606/205
[58] Field of Search .................................. 606/1, 51, 52, 606/174, 205–210

[56] References Cited

U.S. PATENT DOCUMENTS

| | | |
|---|---|---|
| 5,603,711 | 2/1997 | Parins et al. . |
| 5,603,723 | 2/1997 | Aranyi et al. ............................. 606/52 |
| 5,743,906 | 4/1998 | Parins et al. . |
| 6,039,733 | 3/2000 | Buysse et al. ............................. 606/51 |

*Primary Examiner*—Michael Buiz
*Assistant Examiner*—William Lewis
*Attorney, Agent, or Firm*—Nikolai, Mersereau & Dietz, P.A.

[57] ABSTRACT

An endoscopic bipolar forceps comprises an elongated tubular member dimensioned to fit through the working lumen of an endoscope where the tubular member includes a handle at its proximal end and a pair of end effectors at its distal end and with a lumen extending between them. The end effectors each have a metal tissue cutting and tissue sample capturing and retaining element facing one another and capable of being open and closed by manipulating the handle. Each of the end effectors includes an electrode supported by and insulated from it. A push rod coupling the handle to the end effectors for inducing the pivotal movement thereof also serves as an electrical conductor for applying a first potential to the metal tissue cutting and tissue sample capturing and retaining element. A second conductor extends through the lumen of the tubular member and is electrically connected to the electrodes on each of the end effectors. With this arrangement, an electrocautery voltage is developed between an electrode and the metal tissue cutting and tissue sample capturing element that supports that electrode.

4 Claims, 3 Drawing Sheets

BIPOLAR BIOPSY FORCEPS

BACKGROUND OF THE INVENTION

I. Field of the Invention

This invention relates generally to a biopsy instrument for collecting tissue samples through an endoscope, and more particularly to an instrument having bipolar electrodes for providing electrocoagulation to a site where a tissue sample has been taken.

II. Discussion of the Prior Art

In my earlier U.S. Pat. No. 5,603,711 and in a corresponding issued divisional U.S. Pat. No. 5,743,906, there is described a bipolar biopsy device that comprises an elongated tube dimensioned to fit through a working lumen of an endoscope, the tube having a proximal end and a distal end with a lumen extending therebetween. A handle is affixed to the proximal end of the elongated tube and a pair of end effectors are affixed to the distal end of the tube. A mechanical connection is made between the handle and the end effectors to cause them to open and close relative to one another in a scissors-like action. The end effectors each include a jaw member having an annular cutting edge surrounding a cup-like recess such that when a tissue sample to be excised is placed between the open jaws and then the handle is actuated to close them, the annular cutting blades mechanically sever through the tissue and the resulting severed piece of tissue resides in the cup-shape retainer.

In my earlier patents, which are hereby incorporated by reference herein, an insulating substrate is provided on the exterior surface of the annular cutting blades, and metal electrodes are provided on the insulating layer. Electrical conductors extend through the handle and the tubular member and connect to the two electrode surfaces so that when a voltage is applied, via an electrical surgical generator, an electrocautery voltage is developed across the two electrodes that are disposed individually on, but insulated from, the biopsy forceps jaws.

While the endoscopic bipolar biopsy forceps device described in my above-referenced patents simplifies the endoscopic biopsy procedure by obviating the need for frequent instrument exchanges in order to both cut and coagulate, the configuration of the end effectors makes the device more difficult and expensive to manufacture. Specifically, the steps of fitting and bonding the tissue cutting and retention cups within the outer supports while maintaining electrical isolation between the two involves a substantial number of operations and a substantially higher cost of manufacture as compared to a similar instrument made in accordance with the present invention.

It is accordingly a principal purpose of the present invention to provide an improved design for a bipolar biopsy forceps for use in endoscopic procedures.

Another object of the invention is to provide an endoscopic bipolar biopsy forceps that is easier to manufacture than prior art devices designed for the same purpose.

Yet another object of the invention is to provide an improved endoscopic bipolar biopsy forceps in which a coagulating voltage is applied between a metallic tissue cutting and retaining cup and an electrode affixed to the tissue cutting and retaining cup, but with an insulating layer therebetween.

Still another object of the invention is to provide an improved endoscopic bipolar biopsy forceps having applied electrodes and deposited or applied conductors for coupling the electrodes to a power source.

SUMMARY OF THE INVENTION

The present invention is an endoscopic bipolar biopsy forceps of a type having an elongated tubular member having a proximal end, a distal end and a lumen extending between these two ends. A handle member having a stationary element and a movable element is located at the proximal end of the tubular member with the stationary element being affixed to it. At the distal end of the tubular member are first and end effectors that are pivotally coupled to one another with at least one of the first and second end effectors being operatively coupled to the movable element of the handle whereby the first and second end effectors can be opened and closed relative to one another. Each of the end effectors has a tissue cutting element formed from a conductive material and a conductive tissue sample capturing and retaining element that are in facing relation to one another. An electrode is supported by and insulated from the metal tissue cutting element on at least one of the first and second end effectors, and means are provided for applying a coagulating voltage between the electrode and the metal tissue cutting element of the end effector on which the electrode is supported.

The invention can be practiced by including electrodes on both the first and second end effectors where the electrodes are connected to a source of electro-coagulation voltage on the non-facing surfaces of the end effectors.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
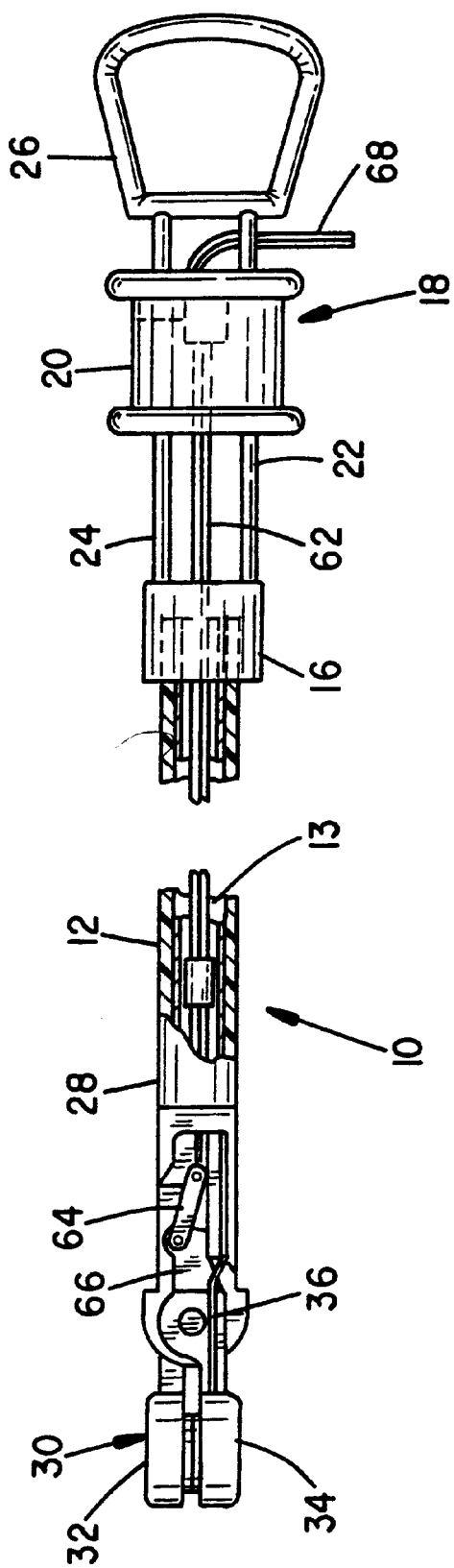
FIG. 1 is a partially sectioned side elevation of an endoscopic bipolar biopsy forceps constructed in accordance with the present invention.

With reference first to FIG. 1, the bipolar biopsy device configured in accordance with the present invention is indicated generally by numeral 10 and comprises an elongated tubular member 12 whose outside diameter is sufficiently small to pass through the working lumen of an endoscope (not shown) where the endoscope further includes illumination fibers and image fibers traversing the length thereof permitting viewing of a surgical site. The elongated tubular body member 12 has a proximal end 14 affixed to a stationary portion 16 of a handle device 18. Slidably mounted on the stationary portion 16 of the handle 18 is a movable spool 20 adapted to slide longitudinally along guides 22 and 24. The stationary portion of the handle also includes a finger loop 26 at the proximal end of the guide rods 22 and 24.

The elongated tubular member 12 also has a distal end 28 to which is attached end effectors, indicated generally by numeral 30 in FIG. 1. As will be explained in detail below, the end effectors 30 comprise a pair of jaw members including jaws 32 and 34, which are pivotally joined together by a rivet 36 that extends through aligned bores 38 and 40 in the jaw members so that the jaws 32 and 34 are free to pivot with respect to one another in a scissors-like action.

Figure 2:
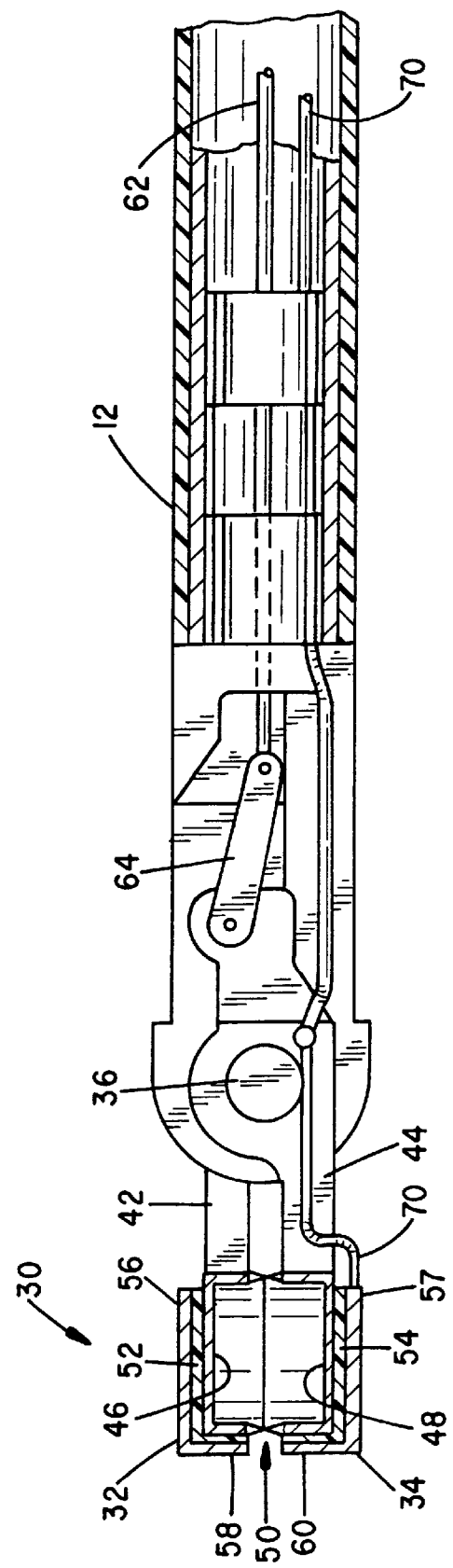
FIG. 2 is a partially sectioned view of the distal end portion of the instrument of FIG. 1.

With reference to FIG. 2, each of the jaw members comprises a shank as at 42 and 44 having an integrally formed, conductive, cup-like receptacle 46 and 48 which may be circular in cross section and whose open ends are defined by a tapered periphery to form a sharp cutting edge, as at 50.

Figure 3:
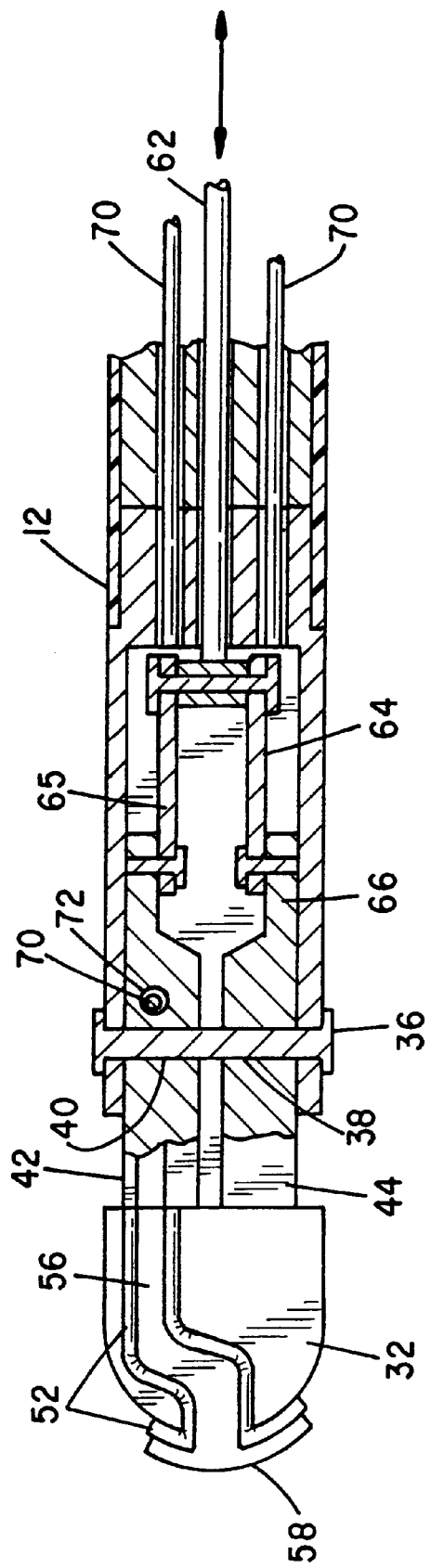
FIG. 3 is a top plan view of the distal end portion of the instrument of FIG. 1.

The outer surface of the tissue collecting cups 46 and 48 are coated or otherwise covered by an insulating layer 52 and 54 and a conductive electrode, as at 56 in FIG. 3, are supported atop the insulating layers 52 and 54 and lead to electrodes 58, 60 formed on the front peripheral surfaces of the jaws, electrode 58, 60 are electrically isolated from the metal cutting edge 50 by the insulating layers.

The movable portion 20 of the handle member 18 is connected by a conductive push rod 62 to a linkage 64 that is pivotally connected to a lever member 66 that forms a part of the jaws 32 and 34. As the movable handle member 20 is reciprocally slid along the guide rods 22 and 24 of the stationary handle member 16, the jaws 32 and 34 are made to open and close relative to one another. The manner in which this is achieved is more fully set forth in my above-referenced U.S. Pat. No. 5,603,711 which has been incorporated by reference and, accordingly, further explanation of the constructional features of the actuating mechanism is believed to be unnecessary. Suffice it to say, the closing of the jaws on a tissue sample results in the sharpened edges 50 of the jaws 32 and 34 cutting through the tissue segment comprising the biopsy specimen with the tissue segment being retained within the confines of the cup members 46 and 48.

To cauterize the site and stem any bleeding, an electrosurgical generator (not shown) is connected, via a cord 68 (FIG. 1), to the instrument 10. Specifically, one of the conductors in the card attaches to the conductive push rod 62 which connects to the jaws 32 and 34. A second conductor 70 also extends through the lumen 13 of the elongated tubular member 12 and bifurcates near its distal end to connect to the metal traces, as at 56 and 57, leading to the electrodes 58 and 60, respectively. Thus, when a foot switch (not shown) associated with the electrosurgical generator is closed, an electrocautery voltage is developed between the electrode 58 and conductive specimen collection cup 46 on which it is mounted. Likewise, an electrocautery voltage is established between the electrode 60 and the conductive cup 48 on which it is mounted. In that each of the cups is at the same electrical potential, no short circuiting takes place when the sharpened cutting edges 50 of each of the jaws come into contact.

While the disclosed embodiment illustrates electrodes on each of the jaws 32 and 34, the invention will work if only a single electrode 58 or 60 is provided on one of the jaws.

Thus, it can be seen that in my earlier designs described in the aforereferenced U.S. patents (page 1, supra), the electrocoagulating current flowed perpendicularly through the tissue sample pinched between the cutting jaws, whereas with the present invention, two current paths flow transversely through the captured tissue from the electrodes to the metal cups on which they reside. The present invention allows better control over the thermal spreading.

The invention described herein is somewhat easier to manufacture than is the device described in my earlier U.S. Pat. No. 5,603,711. First of all, it is not necessary to utilize an insulative pivot member 36 because the conductive specimen retaining cups 46 and 48 can be at the same electrical potential. The insulating material 52 applied to the outer surface of the opposed jaws 32 and 34 may be a ceramic, glass, a high temperature plastic that may be deposited through a mask to provide a desired routing pattern. It may also be molded on or otherwise bonded to the jaws. The conductive electrodes and the metal conductors leading to them may also be applied atop the insulative layer and then electrically connected by the wire 70 at a convenient location along the arm 42 or 44 of the jaws. In the preferred embodiment, this is achieved by providing a bore 72 through the arm 44 so that a bifurcated branch of the conductor 70 can be brought up through the bore to make electrical contact with the conductor 56 on the surface of the arm 42. A similar connection may be made to the electrode 57 on the arm 44 leading to the electrode 60.

The electrode may also be prefabricated as a flexible printed circuit and subsequently bonded in place on the metal end effectors.

It can be seen, then, that the endoscopic biopsy instrument described herein differs from the prior art in that the electrocautery voltage is developed between the inner metal tissue cutting and retention cups and an electrode carried by but insulated from those cups.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An endoscopic bipolar forceps comprising:

(a) an elongated tubular member having a proximal end, a distal end and a lumen extending therebetween;

(b) a handle member having a stationary element and a movable element, the stationary element being affixed to the proximal end of the tubular member;

(c) first and second end effectors pivotally coupled to one another and affixed to the distal end of the tubular member with at least one of the first and second end effectors being operatively coupled to the movable element of the handle for opening and closing the first and second end effectors relative to one another, each said end effector having a metal tissue cutting element and a metal tissue sample capturing and retaining element in facing relation to one another;

(d) an electrode supported by and insulated from the metal tissue cutting element of at least one of the first and second end effectors; and (e) means extending through said lumen for applying a coagulating voltage between the electrode and the metal tissue cutting element of the end effector on which the electrode is supported.

2. The endoscopic bipolar biopsy forceps of claim 1 and further including a further electrode supported by and insulated from the metal cutting element of another of the first and second end effectors and further means extending through said lumen for applying a coagulating voltage between the further electrode and the metal tissue cutting element of the said another of the first and second end effectors.

3. The endoscopic bipolar biopsy forceps of claim 1 wherein the metal tissue cutting element and metal tissue sample capture and retaining element are held at the same first electrical potential, with the electrode being held at a different second potential when the coagulating voltage is applied.

4. The endoscopic bipolar biopsy forceps of claim 2 wherein the metal tissue cutting element and metal tissue sample capturing and retaining element of the first and second end effectors are held at the same first electrical potential, with the electrode and the further electrode being held at a different second potential when the coagulating voltage is applied.

* * * * *